Figure 1:
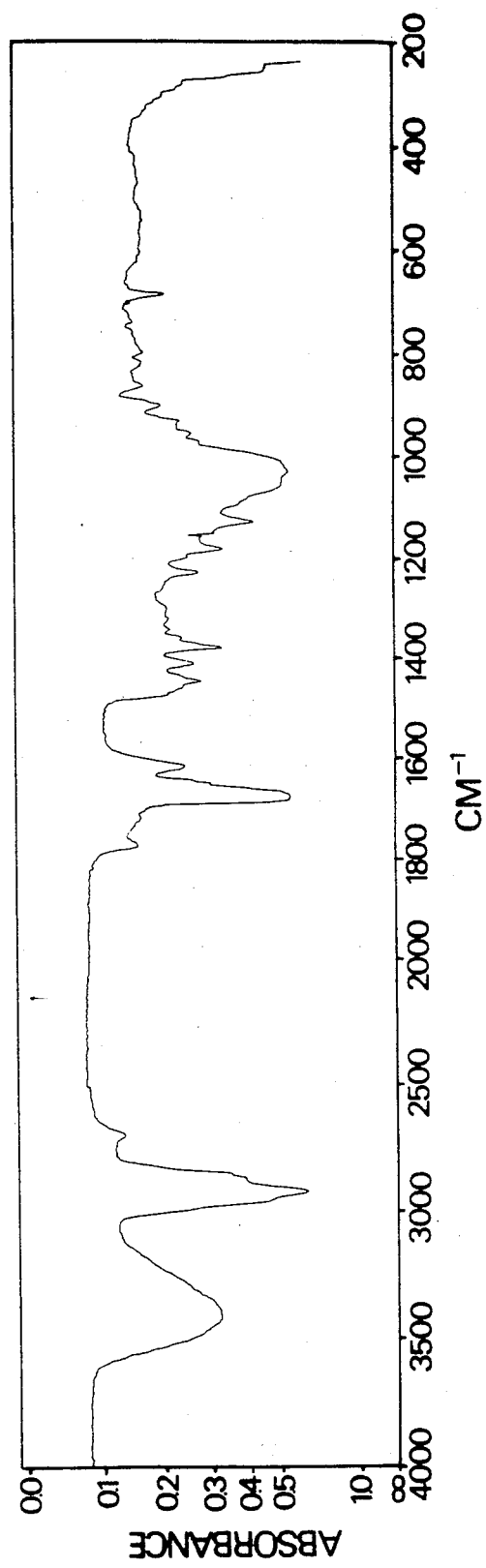

United States Patent [19]

Lorck et al.

[11] Patent Number: 4,576,961

[45] Date of Patent: Mar. 18, 1986

[54] ANTIBIOTIC HETEROCYCLIC OXYGEN COMPOUNDS AND USE

[76] Inventors: Henning O. B. Lorck, No. 4, Rudemarken, DK-2840 Holte; Poul R. Rasmussen, No. 7, Faellesvej, DK-3600 Frederikssund, both of Denmark

[21] Appl. No.: 527,812

[22] Filed: Aug. 30, 1983

Related U.S. Application Data

[63] Continuation-in-part of Ser. No. 322,694, Nov. 18, 1981, abandoned.

[30] Foreign Application Priority Data

Dec. 3, 1980 [GB] United Kingdom ................ 8038772

[51] Int. Cl.$^4$ .................. A61K 31/335; A61K 31/34; C07D 303/32; C07D 493/10
[52] U.S. Cl. ................................. 514/462; 435/123; 435/254; 514/475; 549/332; 549/548
[58] Field of Search ................................ 424/115–122, 424/278, 285; 549/332, 548; 514/462, 475

[56] References Cited

U.S. PATENT DOCUMENTS 3,176,026 3/1965 Steininger et al. .................. 549/332

Primary Examiner—Richard L. Raymond
Attorney, Agent, or Firm—Cushman, Darby & Cushman

[57] ABSTRACT

This invention relates to antibiotic substances, in particular to an antibiotic complex for use in the human and veterinary clinical practice and as an additive in feeds.

8 Claims, 2 Drawing Figures

ANTIBIOTIC HETEROCYCLIC OXYGEN COMPOUNDS AND USE

This is a continuation-in-part of Ser. No. 322,694 filed Nov. 18, 1981, now abandoned.

This invention relates to antibiotic substances. In particular, it relates to an antibiotic complex comprising a group of closely related compounds, this complex arbitrarily designated herein as antibiotic PR-1350 or simply PR-1350, which complex has shown interesting properties in relation to its use in the human and veterinary clinical practice and as an additive in feeds. The invention also relates to the method of producing PR-1350, pharmaceutical preparations containing PR-1350 and methods for producing such preparations, the strains and mutants thereof producing PR-1350 and the use of PR-1350 in the treatment of animals and human beings.

The antibiotic complex PR-1350 is produced by a fungus isolated from an agar plate infection in the antibiotic laboratory at Leo Pharmaceutical Products in connection with isolation of antibiotic-producing fungi. The organism has been taxonomically characterized by Centraalbureau voor Schimmelcultures, Baarn, the Netherlands, as a novel strain of *Oidiodendron truncatum* Barron, and has been deposited there under the designation *Oidiondendron truncatum* Barron, HL-972, ZP-88 under No. CBS 475.78.

Oidiodendron is grouped with the *Fungi imperfecti*. According to N. F. Buchwald: *Fungi imperfecti*, using the classification method of Saccardo, the genus Oidiodendron belongs to the family Dematiaceae and the order Hyphomycetales.

*Oidiodendron truncatum* Barron, HL-972, ZP-88 is being cultured in an aqueous nutrient medium under submerged aerobic conditions until a suitable level of antibiotic activity is obtained. It is to be understood, also, that for the preparation of limited amounts, surface cultures and shaking flasks can be employed. The strain is cultured in a nutrient medium containing a carbon source, e.g. an assimilable carbohydrate, and a nitrogen source, e.g. an assimilable nitrogen compound or proteinaceous material. Preferred carbon sources include glucose, sucrose, glycerol, malt extract, dextrin, and the like. Preferred nitrogen sources include cornsteep liquor, yeast, autolyzed brewer's yeast, soybean meal, cottonseed meal, fish meal, cornmeal, milk solids, pancreatic digest of casein, distiller's soluble, animal peptone liquors, meat and bone scraps, and the like. Combinations of these carbon and nitrogen sources can be used advantageously. Pure "synthetic" media can also be used but often results in lower yields. Trace metals, e.g. zinc, magnesium, manganese, cobalt, iron, and the like, need not be added to the fermentation medium since tap water and unpurified ingredients are used as components of the medium prior to sterilization of the medium.

Production of the complex of the invention can be effected at any temperature conductive to satisfactory growth of the microorganism, e.g. between about 12° and 35° C., and more particularly, between about 14° and 30° C., and preferably between about 16° and 24° C. The pH of the medium is maintained at values which are conductive to satisfactory growth of the microorganism, e.g. between pH 4.0 to 8.0, preferably between pH 5.0 to 7.0. Ordinarily, optimum production of the complex is obtained in about 2 to 10 days, dependent upon the nutrient medium and the fermentation conditions used. When growth is carried out in large fermentors, it is preferable to use the vegetative form, rather than the spore form, of the microorganism for inoculation to avoid a pronounced lag in the production of the new complex and the attendant ineffective utilization of the equipment. Accordingly, it is desirable to produce a vegetative inoculum in a nutrient broth culture by inoculating this broth culture with an aliquot from a slant culture. When a young, active vegetative inoculum has thus been secured, it is transferred aseptically to large fermentors. The medium in which the vegetative inoculum is produced can be the same as, or different from, that utilized for the production of the new compounds, as long as it is such that a good growth of the microorganism is obtained.

It is to be understood that the microbiological process disclosed herein, though described in detail with reference to *Oidiodendron truncatum* Barron strain HL-972 ZP-88 CBS 475.78, is not limited to this particular microorganism. It is intended that this invention also include other strains or mutants of the said microorganism which can be produced by procedures well known in the art, e.g. by subjecting the novel microorganism to X-ray or ultraviolet radiation, nitrogen mustard, phage exposure, and the like.

Furthermore, other strains of *Oidiodendron truncatum* Barron, which, although they are known and available, were not known, prior to the subject invention, to produce antibiotics, now have been shown to produce the antibiotic PR-1350 complex, providing the right fermentation conditions are used.

These strains are available at Centraalbureau voor Schimmelcultures, Baarn, the Netherlands, under the numbers CBS 629.70, CBS 222.65, CBS 115.65 and CBS 114.65.

Following the production of the antibiotic complex PR-1350 a variety of procedures can be employed in the isolation and purification of the compounds of the subject invention, e.g. solvent extraction, partition chromatography, silica gel chromatography, liquid-liquid distribution in a Craig apparatus, absorption on resins, crystallization from solvents, or other methods commonly employed in the fermentation art. Since the majority of antibiotic activity is associated with the broth, a preferred method of recovery is filtration of the fermentation medium and absorption of the active principle onto a macroreticular resin such as Amberlite ®XAD-2 or Diaion ®HP-20 at a pH-value between 2 and 10, followed by elution with an organic solvent and evaporating the eluent in vacuo. Methanol is a particularly useful eluting solvent for this procedure. Alternatively, the antiobiotic PR-1350 complex can be extracted from the broth with a suitable organic solvent at a pH-value between 2 and 10. The resulting extract is treated with a drying agent and then concentrated to give the crude product. Solvents of medium polarity such as ethyl ether, ethyl acetate, benzene or chloroform are preferred for this extraction.

The PR-1350 antibiotic complex can be further purified by chromatography, e.g. on Diaion ®HP-29 using e.g. methanol-water mixtures as eluents, or on Sephadex ®LH-20 using e.g. methanol or chloroform-methanol-hexan mixtures as eluents.

Antiobiotic PR-1350 is a white, amorphous solid, the elementary analysis of which shows the absence of nitrogen, phosphorus, sulphur, chlorine, and bromine. The dominating peak in the field ionization mass spectrum of the complex is found at m/e 366. High resolution electron impact mass spectrometry shows this peak to be associated with the formula $C_{20}H_{30}O_6$. Other prominent peaks in the electron impact mass spectrum are listed in Table A.

TABLE A

Characteristic peaks from the electron impact mass spectrum of PR-1350 complex

| m/e | Formula |
|---|---|
| 366 | $C_{20}H_{30}O_6$ |
| 205 | $C_{14}H_{21}O$ |
| 204 | $C_{14}H_{20}O$ |
| 189 | $C_{14}H_{21}$ and $C_{13}H_{17}O$ |
| 187 | |
| 175 | |
| 161 | |
| 159 | |
| 149 | |
| 147 | |
| 145 | |
| 135 | |
| 133 | |
| 131 | |
| 121 | |
| 119 | |
| 109 | |
| 107 | |
| 105 | |
| 95 | |
| 93 | |
| 91 | |
| 81 | |
| 79 | |
| 77 | |
| 69 | |
| 67 | |
| 55 | |
| 44 | |
| 41 | |

The PR-1350 complex is soluble in common organic solvents, such as ethyl acetate, ethyl ether, benzene, ethanol, methanol, chloroform and the like, but is relatively insoluble in water and insoluble in saturated hydrocarbon solvents.

A solution of PR-1350 complex in ethanol shows an UV maximum, $\lambda$ max, at 230 nm ($E_1$ $_{cm}$$^{1\%}$=304). The IR-spectrum of the PR-1350 complex (KBr pellet) is shown in the accompanying drawing FIG. 1, whereas in table B and C are listed some characteristic absorptions, seen in the $^1H$ and $^{13}C$-NMR-spectra of the complex. The NMR-spectra were recorded on a JEOL FX 100 spectrometer at 99.6 megacycles on a 10% solution in deuterochloroform or deuteroacetone. Chemical shifts are given in ppm ($\delta$-scale) with tetramethylsilane as a reference.

TABLE B

Characteristic signals in the $^1H$—NMR-spectrum of antibiotic PR-1350 complex (in deuteroacetone)

| Chemical shift | Multiplicity | Relative intensity |
|---|---|---|
| 9.28 | s | 1 |
| 6.63* | broad t | 1 |
| 2.41 | m | 2 |
| 1.77 | m | |
| 1.21 | s | |
| 0.96 | s | |

*This signal appears at 6.54 when the spectrum is run on a solution of PR-1350 complex in deuterochloroform.

TABLE C

Characteristic signals in the $^{13}C$—NMR-spectrum of antibiotic PR-1350 complex (in deuterochloroform)

| Chemical shift | Multiplicity |
|---|---|
| 193.8 | d |
| 151.9 | s |
| 151.5 | d |
| 44.1 | |
| 37.6 | |
| 36.3 | |
| 29.3 | |
| 28.6 | |
| 25.9 | |
| 21.6 | |
| 17.8 | |
| 15.8 | |

The optical rotation of a solution of PR-1350 complex may change during the first few hours after the preparation of the solution, the initial value being dependent on the method of isolation of the complex, whereas the final value is independent of such factors. Typical values for two different charges of the complex are shown in table D

TABLE D

The specific rotation of PR-1350 complex (c. 1, ethanol)

| | Time after preparation of the solution (hours) | $[\alpha]_D$ |
|---|---|---|
| charge a | 0 | +82.1 |
| | 1 | +85.6 |
| | 2 | +86.5 |
| | 3 | +86.6 |
| | 4 | +86.6 |
| charge b | 0 | +72.0 |
| | 1 | +80.0 |
| | 2 | +85.0 |
| | 3 | +85.5 |
| | 4 | +85.6 |

The components of the PR-1350 complex can be separated by chromatography on Sephadex ®LH-20 using chloroform-methanol-hexan (65:10:25) as eluent, but upon standing in solution, the separated components are rapidly transformed to the complex again as seen by repeated chromatography (see Example 9 for details).

When the PR-1350 complex is dissolved in methanol and left in the refrigerator for several days a crystalline hemiacetal is precipitated. This compound which also forms part of this invention is called PR-1381. It has a melting point of 139°–141° C. and shows an UV-maximum, $\lambda$ max, at 230 nm ($E_1$ $_{cm}$$^{1\%}$=310; Ethanol). The IR-spectrum of PR-1381 (KBr-pellets) is shown in the accompanying drawing FIG. 2.

The field ionization and electron impact mass spectra of PR-1381 are identical with those of PR-1350.

Characteristic signals seen in an $^1H$-NMR-spectrum recorded immediately after dissolution of PR-1381 in deuterochloroform are listed in table E.

When the solution in deuterochloroform is allowed to stand at room temperature, these initial signals gradually disappear while methanol is liberated from the molecule, and finally after 10 hours, a spectrum is observed which is identical with that obtained from PR-1350 complex in deuterochloroform, except for an extra signal at $\delta$=3.48, probably due to methanol liberated during the transformation of PR-1381 to the PR-1350 complex.

TABLE E

Characteristic signals in the $^1$H—NMR-spectrum of PR-1381, recorded immediately after preparation of a solution in deuterochloroform

| Chemical shift | Multiplicity | Relative intensity |
|---|---|---|
| 9.28 | s | 1 |
| 6.54 | t | 1 |
| 5.31 | broad s | 1 |
| 4.58 | t | 1 |
| 3.40 | s | 3 |
| 3.25 | d (J = 4.5) | 1 |
| 2.82 | d (J = 4.5) | 1 |
| 2.35 | m | 2 |
| 1.77 | m |  |
| 1.21 | s | 3 |
| 1.00 | d (J = 6) | 3 |
| 0.90 | s | 3 |

It thus appears that PR-1381 in solution decomposes to the PR-1350 complex with liberation of methanol. This is further corroborated by the finding that the antimicrobial effect of PR-1381 qualitatively and quantitatively is identical with that of the PR-1350 complex, and by the data for the optical rotation of PR-1381 as a function of time, which is given in table F.

TABLE F

Specific rotation of PR-1381 (c. 0.2 ethanol)

| Time after preparation of the solution (hours) | $[\alpha]_D$ |
|---|---|
| 0 | +102.8 |
| ½ | +97.2 |
| 1 | +94.0 |
| 2 | +91.6 |
| 10 | +89.6 |

It is seen from the tab that although the initial value is quite different from those given in table D for the PR-1350 complex, the final values in the two tables are in fair agreement.

Hemiacetals corresponding to PR-1381 can be obtained by reacting PR-1350 complex with other alcohols than methanol with or without a solvent, such alcohols being of the general formula ROH, in which R stands for a straight or branched alkyl radical having from 1 to 8 carbon atoms, such as methy, ethyl, propyl, isopropyl, butyl, isobutyl, tert-butyl, the known isomers of pentyl, hexyl, heptyl and octyl, such alkyl radicals being optionally substituted with halogen atoms or hydroxy, alkyloxy, aralkyloxy, aryloxy, alkanoyloxy, aralkanoyloxy, aroyloxy, sulfhydryl, alkylthio, aralkylthio, arylthio, alkanoylthio, aroylthio, azido, nitro, cyano, thiocyano, hydroxycarbonyl, alkyloxycarbonyl, aryloxycarbonyl, amino, alkylamino, dialkylamino, arylamino, alkanoylamino, and aroylamino groups; R can further be an alkenyl or alkynyl radical having from 2 to 6 carbon atoms, such as allyl, crotyl or propargyl, a cycloalkyl radical having from 3 to 7 carbon atoms in the alicyclic ring, such as cyclopropyl, cyclobutyl, cyclopentyl, cyclohexyl, cycloheptyl, or the mono- or dihalo, lower alkyl, lower alkoxy or hydroxy substituted analogues, an aralkyl, heterocyclylalkyl or aryl radical, such as benzyl, phenylethyl, phenyl or furfuryl, these radicals being optionally substituted with halogen, nitro, lower alkyl, hydroxy or alkoxy radicals.

Like PR-1381 the compounds obtained by such a reaction are antibiotically active and are within the scope of the invention.

On the basis of the above data the following basic structure was ascribed to PR-1350 (I) and the formula II to PR-1381.

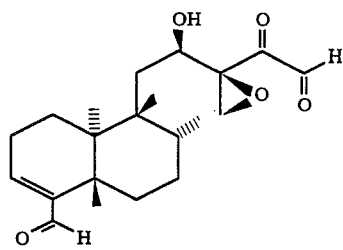

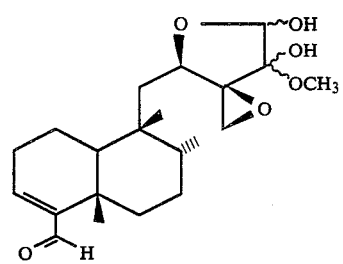

The formulas I and II are meant only to show the relative not the absolute stereochemistry of the compounds.

In solution PR-1350 does not exist exclusively in the form shown in formula I, but is extensively modified as a result of the formation of hemiacetal bonds similar to the one present in formula II.

Furthermore, these hemiacetal forms being formally α-hydroxyketones are capable of forming di- or polymers as described for other α-hydroxyketones in for instance K. Sato, H, Adachi, T. Iwaki and M. Ohashi, J. Chem. Soc. PI (1979) 1806, or B. Gold and T. Leuschen, J. Org. Chem. 46 (1981) 1372, thus further complicating the appearance of the compound.

The in vitro antimicrobial activity of the PR-1350 complex has been determined against a number of test organisms, by standard broth dilution and agar-dilution assays. The minimal inhibitory concentration (MIC) are summarized in the below Table G:

TABLE G

In Vitro Antibacterial Activity of Antibiotic PR-1350 Complex

| Organism | Strain* | MIC μg/ml |
|---|---|---|
| Staphylococcus aureus | CJ | 0.1 |
| Staphylococcus aureus | CJ85 | 0.1 |
| Staphylococcus aureus (Pen. Strep.-resist.) | CJ9 | 0.1 |
| Staphylococcus aureus (Pen. Strep. Tetrac. Eryt. Methic.-Resist.) | CJ110 | 0.1 |
| Diplococcus pneumonia | EA | 0.3 |
| Streptococcus pyogenes NCTC8198 | EC | 0.1 |
| Streptococcus faecalis ATCC8043 | EI3 | 0.3 |
| Corynebacterium xerosis NCTC9755 | FF | 0.03 |
| Listeria monocytogenes NCTC7973 | FT | 0.1 |
| Erysipelothrix insidiosa NCTC8163 | FU | 0.1 |
| Bacillus subtilis | KA2 | 0.1 |
| Pseudomonas aeruginosa | BA2 | 10 |
| Pseudomonas aeruginosa (Ps18s) | BA14 | 30 |
| Pseudomonas aeruginosa (mcPhillip) | BA15 | 10 |
| Pseudomonas stutzeri | BC | 3 |
| Vibrio comma NCTC8367 | BQ | 0.03 |
| Alcaligenes faecalis | GA | 1 |
| Escherichia coli | HA | 3 |
| Escherichia coli | HA2 | 10 |
| Escherichia coli | HA11 | 10 |

TABLE G-continued

In Vitro Antibacterial Activity of Antibiotic PR-1350 Complex

| Organism | Strain* | MIC μg/ml |
|---|---|---|
| Escherichia coli B AS19 | HA47 | 0.3 |
| Escherichia coli W 3110 R⁻ | HA58 | 3 |
| Klebsiella pneumoniae | HE | 3 |
| Klebsiella pneumoniae ATCC10031 | HE4 | 0.3 |
| Klebsiella pneumoniae ATCC10237 | HE7 | 10 |
| Klebsiella aerogenes 1082E | HC7 | 10 |
| Enterobacter cloacae P99 | HC8 | 10 |
| Serratia marcescens ATCC14756 | HG4 | 10 |
| Proteus vulgaris ATCC13315 | HJ | 3 |
| Proteus mirabilis | HJ3 | 10 |
| Salmonella paratyphi A NCTC8002 | HK | 30 |
| Salmonella schotmuelleri NCTC5704 | HL | 30 |
| Salmonella typhimurium NCTC5710 | HL2 | 10 |
| Salmonella abortus-equi NCTC5727 | HL3 | 3 |
| Salmonella hirschfeldii NCTC5733 | HM | 1 |
| Salmonella cholerae-suis NCTC5735 | HM2 | 10 |
| Salmonella typhosa NCTC5760 | HN | 3 |
| Salmonella enteritidis NCTC3045 | HN2 | 10 |
| Shigella dysenteriae NCTC82171 | HR | 10 |
| Shigella flexneri NCTC 8192 | HT | 3 |
| Yersenia enterocolitica | HY | 3 |
| Bacteroides fragilis | JA2 | 1 |
| Chromobacterium violaceum NCTC9371 | LQ | 0.3 |
| Neisseria gonorrhoeae (Sulfathiaz. Resist.) | DA2 | 1 |
| Neisseria gonorrhoeae | DA3 | 0.3 |
| Neisseria gonorrhoeae (Pen. resist.) | DA9 | 0.3 |
| Neisseria gonorrhoeae (Pen. resist.) | DA40 | 0.3 |
| Neisseria meningitidis NCTC8365 | DB | 0.1 |
| Haemophilus influenzae NCTC 6489 | IX3 | 3 |
| Haemophilus influenzae | IX5 | 0.1 |
| Haemophilus influenzae ATCC9007 | IX12 | 3 |
| Haemophilus influenzae (Ampicillin Resist.) | IX23 | 1 |
| Haemophilus influenzae (Ampicillin Resist.) | IX29 | 3 |
| Haemophilus parahaemolyticus | IX7 | 1 |
| Bordetella pertussis | IY3 | 3 |
| Propionibacterium acnesNCTC737 | FN | 3 |
| Mycobacterium paratuberculosis NCTC 6926 | MD | 3.2 |
| Mycobacterium phlei | MO | 1.0 |
| Candida albicans ATCC10231 | ZA | >100 |
| Candida albicans | ZA2 | >100 |
| Candida parakrusei | ZA3 | >100 |
| Candida guilliermondii CBS566 | ZA6 | >100 |
| Candida pseudotropicalis CBS607 | ZA11 | >100 |
| Candida tropicalis CBS 94 | ZA13 | >100 |
| Saccharomyces ellipsoideus | ZZ | >100 |
| Aspergillus fumigatus CBS | ZM | >100 |
| Trichophyton mentagrophytes CBS | ZO | >100 |
| Trichophyton mentagrophytes var. interdigitale CBS | ZO2 | >100 |
| Trichophyton rubrum ATCC10272 | ZO7 | >100 |
| Trichophyton schonleini | ZO10 | >100 |
| Tetrahymena pyriformis CU-1630/1-W | | 10 |

*Numbers refer to the Leo Pharmaceutical Products' Culture Collection

PR-1350 does not show cross resistance with any of the antibiotics used in medicine, such as pencillins, cephalosporins, aminoglycosides, tetracyclines, fusidic acid, chloramphenicol, erythromycin, Novobiocin or lincomycins.

PR-1350 has shown strong bactericidal effects towards all bacteria mentioned in Table G.

Furthermore, PR-1350 has been shown to possess antitumor activity in mice. Thus, when PR-1350 was administered intraperitoneally on 9 consecutive days (1-9) at four levels to mice inoculated intraperitoneally with $10^6$ P-388 leukemia cells on day 0 a significant inhibition of the tumor was observed at all doses as shown in table H.

TABLE H

Activity of PR-1350 against P-388 lymphocytic leukemia in the mouse

| Dose (mg/kg) | T/C$^{(x)}$ |
|---|---|
| 250 | 200 |
| 125 | 164 |
| 62.5 | 160 |
| 31.25 | 163 |

$^{(x)}$T/C is the ratio of the average survival time of treated mice (6 mice per dose level) to that of untreated controls in percent. Activity is defined as values of T/C ≧ 125.

PR-1350 has been shown to interfere with the synthesis of DNA in bacterial cultures.

An exponentially growing culture of Staphylococcus aureus was divided into two subcultures, one of which were treated with 2.5 μg/ml PR-1350. In the following 2 generations the synthesis of DNA, RNA, and Protein was followed in the two cultures.

The results are shown in the Table J.

TABLE J

Relative synthesis of DNA, RNA, and Protein is PR-1350 treated and untreated cultures of Staphylococcus aureus

| | |
|---|---|
| Relative synthesis of DNA (Percent) | 20 |
| Relative synthesis of RNA (Percent) | 90 |
| Relative synthesis of Protein (Percent) | 95 |

It appears that PR-1350 inhibits DNA synthesis, but leaves RNA and Protein synthesis virtually unhampered.

The activity of PR-1350 may thus be related to its ability to interfere specifically with cellular DNA-synthesis. This mechanism of action makes PR-1350 useful in the treatment of a variety of proliferative disorders, such as psoriasis.

The compounds of the invention have shown a low degree of toxicity in mice and in rats. It is known that an isolate from the culture of a strain of Oidiodendron truncatum Barron possesses an antibacterial and fungicidal activity (Marchisio, Abstracts of Mycology, [Vol. 12(5)] 4, 50697, from Allionia 21,67,1976). The author indicates this activity to be of the same discrete magnitude against Staphylococcus aureus as against Escherichia coli and to be of high magnitude against the yeast fungus Candida albicans. The author concludes that the active principle seems to correspond to the antibiotic Fuscin, produced by Oidiodendron fuscum Robak, described by S. E. Michael (Biochem. J. 43,528,1948).

From the above antibiotic spectrum provided for PR-1350 it appears that PR-1350 shows a high activity against Staphylococcus aureus, a 10-100 times lesser activity against Escherichia coli and no activity at all against Candida albicans. Thus, it will be obvious that the antibiotic principle described by Marchisio is different from PR-1350.

It is a further object of the present invention to provide pharmaceutical compositions which are useful in the treatment of infectious diseases in the human and veterinary practice.

With this object in view, the compositions of the invention contain as an active component PR-1350, or a hemiacetal thereof, e.g. PR-1381, together with solid or liquid pharmaceutical carriers and/or diluents.

In the said compositions, the ratio of therapeutically active material to carrier substance can vary between 1% and 95% by weight. The compositions can be worked up to various pharmaceutical forms of presentation, such as granulate, tablets, pills, dragees, suppositories, capsules, sustained-release tablets, suspensions, injection medicine, or as far as mixtures are concerned, they may be filled in bottles or tubes or similar containers. Pharmaceutical organic or inorganic, solid or liquid carriers and/or topical administration can be used to make up compositions containing the present compounds. Water, gelatine, lactose, starch, magnesium stearate, talc, vegetable and animal oils and fats, benzyl alcohol, gum, polyalkylene glycol, petroleum jelly, cocoa butter, lanolin or other known carriers for medicaments are all suitable, while stabilizing agents, wetting and emulsifying agents, salts for varying the osmotic pressure or buffers for securing an adequate pH-value of the composition can be used as auxiliary agents.

Furthermore, the composition may contain other pharmaceutically active components which can appropriately be administered together with PR-1350 or a hemiacetal thereof in the treatment of infectious diseases, such as other suitable antibiotics, in particular such agents, which may enhance the activity and/or prevent development of resistance. Other compounds which advantageously may be combined with the compounds of the invention, especially in topical preparations, include e.g. corticosteroids, like hydrocortisone, triamcinolone or fluocinolone.

For granulates, tablets, capsules or dragees, the pharmaceutical composition of the invention appropriately contains from 25 percent to 95 percent of the compounds of the invention, and in oral suspensions the corresponding amount is appropriately from 2–25 percent.

For parenteral use, the compounds of the invention are preferably given by injection of pharmaceutical compositions containing from 1 to 20 percent of the active ingredient.

As indicated above, the present compounds may be worked up to pharmaceutical forms of presentation including suspensions, powders, ointments and creams. A pharmaceutical preparation for oral treatment may also be in the form of a suspension containing the compounds in an amount of from 20 to 100 mg per ml of vehicle. A pharmaceutical preparation for topical treatment may be in the form of a powder, an ointment, a cream or a lotion containing the compounds of the invention in an amount of from 0.5 l to 10 g per 100 g of preparation.

Another object of the invention resides in the selection of a dose of the compounds of the invention, which dose can be administered so that the desired activity is achieved without simultaneous secondary effects. In the human therapy, the compounds of the invention is conveniently administered (to adults) in dosage units containing not less than 50 mg and up to 1000 mg, preferably from 250 to 750 mg.

By the term "dosage unit" is meant an unitary, i.e. a single dose which is capable of being administered to a patient, and which may be readily handled and packed, remaining as a physically stable unit dose comprising either the compounds as such or a mixture with solid or liquid pharmaceutical diluents or carriers.

In the form of a dosage unit, the compounds may be administered once or more times a day at appropriate intervals, always depending, however, on the condition of the patient, and in accordance with the prescription made by the medical practitioner.

Thus in systemic treatment a daily dose will be from 0.25 g to 4 g per day, preferably an amount of from 0.5 to 3 g.

By the term "dosage unit" is in connection with the topical use meant a unitary, i.e. a single dose capable of being administered topically to the patients and applicating per sq. centimeter of the infected area from 0.1 mg to 10 mg and preferably from 0.2 mg to 1 mg of the compounds.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response in the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components, as mentioned hereinbefore.

Still another object of the invention is to provide a method of treating patients suffering from infectious diseases, the method comprising administering to patients from 0.25 g to 4 g per day, preferably from 0.5 g to 3 g per day. Preferably, the compound is given in the form of the dosage units aforesaid.

The invention will be further described in the following Examples which are not construed as limiting the invention.

EXAMPLE 1

To achieve vegetative growth, spores of *Oidiodendron truncatum* Barron, strain HL-972 ZP-88 from a 10 days' old agar slant was transferred to 500 ml Erlenmeyer flasks containing a sterile broth medium (100 ml) of the following composition:

Corn steep liquor: 20 g per liter
$KH_2PO_4, 2H_2O$: 10 g per liter
$MgSO_4, 7H_2O$: 0.5 g per liter
Sucrose: 50 g per liter
Tap water: ad 1000 ml (pH 6.7)

and the culture was aerobically incubated at 28° C. for 3 days on a reciprocating shaker. The seed material thus obtained was transferred to 2 l shake flasks containing 250 ml of a nutrient medium of the below composition and operating with an inoculum concentration of 8 percent:

Malt extract: 20 g per liter
Sucrose: 20 g per liter
Soy bean meal; 7.5 g per liter
Meat and bone meal: 7.5 g per liter
$K_2HPO_4$: 1 g per liter
Tap water: ad 1000 ml (pH 6.2)

The fermentation takes place on a reciprocating shaking table (112 oscillations per minute) at 28° C. and at a pH of about 6.0 in the nutrient medium. The antibiotic activity was assayed throughout the fermentation by using a disc plate method with a number of test organisms, as indicated in the following Table I:

TABLE I

| Test organism | mm inhibition zone | |
|---|---|---|
| | 2 days | 6 days |
| *Streptococcus pyogenes* | 28 | 33 |
| *Staphylococcus aureus* | 32 | 36 |
| *Corynebacterium xerosis* | 33 | 37 |
| *Escherichia coli* | trace | (16) |
| *Klebsiella pneumoniae* | 17 | 20 |
| *Pseudomonas aeruginosa* | 17 | 20 |
| *Neisseria gonorrhoeae* | 35 | 39 |
| *Candida albicans* | 0 | 0 |
| *Tricophyton mentagrophytes* | 0 | 0 |
| *Aspergillus clavatus* | 0 | 0 |

EXAMPLE 2

To achieve vegetative growth, spores of *Oidiodendron truncatum* Barron, strain HL-972 ZP-88 from a 10 days' old agar slant was transferred to 2 l shaking flasks (1. generation) containing a sterile broth medium (250 ml) of the following composition:

Corn steep liquor: 20 g per liter
Sucrose: 50 g per liter
$KH_2PO_4$, $2H_2O$: 10 g per liter
$MgSO_4$, $7H_2O$: 0.5 g per liter
Tap water: ad 1000 ml (pH 6.7)

and the culture was aerobically incubated at 20° C. for 3 days on a reciprocating shaker. The seed material thus obtained was transferred to a number of culture vessels (2. generation) containing the same broth medium as for the 1. generation. The fermentation of this vegetative stage is carried out under aerobic conditions and with agitation at a temperature of 20° C. for 2 days.

In a 1.5 $m^3$ stainless steel vessel, culture medium (1.0 $m^3$) of the below composition was mixed:

Malt extract: 20 g per liter
Sucrose: 20 g per liter
Soy bean meal: 7.5 g per liter
Meat and bone meal: 7.5 g per liter
$K_2HPO_4$: 1 g per liter
Tap water: ad 1000 ml which before sterilization had been adjusted to a pH value of 6.0, was sterilized at a temperature of 120° C. for 45 minutes, and after cooling to 20° C., it was inoculated with the 2. generation in a concentration of 3 percent. During fermentation, sterile air is passed through the medium in an amount of 0.8 $m^3$ per minute with agitation (110 rpm). The fermentation was continued for 70 hours. The foaming tendency was controlled by using silicone as anti-forming agent. The pH value was maintained at 6.0 throughout the fermentation by the addition of phosphoric acid. The antibiotic activity of culture samples was determined throughout the fermentation by measuring the inhibition zone produced in the agar cup method with *Staphylococcus aureus* as test organism.

EXAMPLE 3

Isolation of Antibiotic PR-1350 complex

Fermentation broth prepared as described in Example 2 was filtered using kieselguhr as a filter aid. The filtrate (900 liters) was passed at a rate of 2 liters/minute through a column prepared from 4.4 liters of Diaion ®HP-20 (height: 56 cm, diameter: 10 cm; the resin was treated before use with water, 2N aqueous sodium hydroxide, water, methanol, 2N aqueous hydrogen chloride, water, methanol, and water). The column was washed with water (20 liters), 25% aqueous methanol (12 liters), 50% aqueous methanol (12 liters), and 75% aqueous methanol (12 liters), and was then eluted with methanol. Fractions containing 2 liters were collected. Fractions 2–7 which contained the majority of the antibacterial activity were combined and evaporated in vacuo. The residue was extracted with 400 ml of methanol, and after filtration the methanol was evaporated. The residue was dissolved in methanol (50 ml), and ether (800 ml) was added to the stirred solution. The precipitate which formed was filtered off, and the filtrate was concentrated in vacuo to an oil which was dissolved in methanol (20 ml) and submitted to column chromatography on 600 ml of Diaion ®HP-20 (height: 90 cm, diameter: 2.9 cm). The active fractions, eluted with methanol-water (95:5), were combined and concentrated in vacuo to an oil (10.1 g).

5.7 g of this crude product was dissolved in methanol (10 ml) and applied to a column of Sephadex ®LH-20 (height: 90 cm, diameter: 29 cm), and the column was eluted with methanol. Active fractions (150 ml) were collected and evaporated to dryness in vacuo to yield 4.2 g of an oil, which was dissolved in a mixture of ether (100 ml) and cyclohexane (200 ml). The solution was treated with 3 g of Norit ®, filtered, and evaporated in vacuo to a volume of 50 ml. 200 ml of cyclohexane was added with stirring, and the precipitate which formed were filtered off, washed with cyclohexane and dried to yield the antibiotic complex as a colourless amorphous powder.

Concentrating the mother liquor to 50 ml and filtrating gave a further amount of the complex.

EXAMPLE 4

Tablets, each containing 250 mg of PR-1350

Ingredients:
PR-1350: 250 g
Lactose: 165 g
Polyvinylpyrrolidone: 7 g
Corn starch: 50 g
Talc: 25 g
Magnesium stearate: 3 g The PR-1350 and the lactose are screened through a 20 mesh sieve and mixed together for 15 minutes. Thereafter the mixed powders are wetted with a solution of polyvinylpyrrolidone in water. The moist mass is passed through a 10 mesh screen and then dried at 38° C. When the moisture has evaporated, the granules are broken on a 16 mesh sieve and mixed with corn starch, talc and magnesium stearate. The granulate is compressed into tablets of 0.50 g, weight using 16/32" punches and dies, yielding 1000 tablets each containing 250 mg of PR-1350.

EXAMPLE 5

Capsules, each containing 250 mg of PR-1381

Ingredients:
PR-1381: 250 g
Starch: 27 g
Magnesium stearate: 3 g

The ingredients are passed through a 60 mesh sieve and mixed for 15 minutes. The mixture is filled into gelatine capsules, using a semi-automatic capsule-filling machine shaken by vibrator. Each capsule contains 280 mg of the mixture corresponding to 250 mg of PR-1381.

EXAMPLE 6

Ointment containing 10 mg PR-1350 per g

Ingredients:
PR-1350: 10 g
Cholesterol: 30 g
Stearyl alcohol: 30 g
Butylhydroxyanisole: 0.1 g
White wax: 80 g
White petrolatum: 850 g The stearyl alcohol, white wax and white petrolatum are melted together on a steam bath. Thereafter the cholesterol and the butylhydroxyanisole are added and dissolved in the melted mixture which is then stirred until cold. The PR-1350 is sieved through a 80 mesh sieve and triturated gradually with the ointment base.

EXAMPLE 7

Isolation of Antibiotic PR-1350 complex

Fermentation broth prepared as described in Example 1 was filtered using kieselguhr as a filter aid. The filtrate (4 liters) was extracted with two portions of ethyl ether (2×1 liter). The combined organic phases were washed with water, dried and evaporated in vacuo to give a crude product, which was further purified by chromatography on Diaion ®HP-20 using methanol-water as an eluent, followed by chromatography on Sephadex ®LH-20 with methanol as the eluent, and finally by precipitation from ether-cyclohexane as described in details in Example 3.

EXAMPLE 8

Preparation of PR-1381

A solution of PR-1350 complex (100 mg), prepared as described in Example 3, in methanol (0.3 ml) was left at 5° C. During 72 hours, crystals precipitated slowly from the solution. Diisopropyl ether (5 ml) was then added, and the crystals were collected by filtration, washed with diisopropyl ether and dried to yield PR-1381, melting point 139°–141° C.

EXAMPLE 9

Separation of the Components in the PR-1350 Complex

A.

300 mg of the PR-1350 complex, prepared as described in Example 3, was submitted to chromatography on a column of Sephadex ®LH-20 (height: 90 cm, diameter: 2.9 cm) using chloroform-methanol-hexan (65:10:25) as an eluent. The first 280 ml of the eluate were collected in one portion, and thereafter fractions of 15 ml were collected. 10 µl portions of each fraction were diluted with 1 ml of methanol and tested for activity against Staphylococcus aureus by the agar cup method. The results are given in the table.

| Fraction number | Zone of inhibition |
| --- | --- |
| 1 | 24 |
| 2 | 23 |
| 3 | 29 |
| 4 | 35 |
| 5 | 33 |
| 6 | 33 |
| 7 | 28 |
| 8 | 32 |
| 9 | 31 |
| 10 | 30 |
| 11 | 32.5 |
| 12 | 32 |
| 13 | 32 |
| 14 | 31.5 |
| 15 | 31 |
| 16 | 26 |
| 17 | 21 |
| 18 | 0 |
| 19 | 0 |

B.

Fractions numbered 4–6 from part A of this Example were pooled and evaporated in vacuo to yield 100 mg of an oily residue, which was again applied to the Sephadex ®LH-20 column used in part A, and the column was eluted with chloroform-methanol-hexane (65:10:25). After collecting the first 300 ml of the eluate in one portion, fractions of 12 ml were collected. The fractions were analyzed for antistaphylococcal activity by the method described in part A of this Example. The results are listed in the table.

| Fraction number | Zone of inhibition |
| --- | --- |
| 1 | 22 |
| 2 | 28 |
| 3 | 31.5 |
| 4 | 30 |
| 5 | 29 |
| 6 | 27.5 |
| 7 | 21 |
| 8 | 24 |
| 9 | 26 |
| 10 | 22 |
| 11 | 21 |
| 12 | 21 |
| 13 | 19 |
| 14 | 18 |
| 15 | 20 |
| 16 | 24 |
| 17 | 29 |
| 18 | 21 |
| 19 | 16 |
| 20 | 0 |

C.

Fractions number 11–15 from part A of this Example were pooled and evaporated in vacuo to yield 175 mg of an oily residue, which was applied to the same Sephadex ®LH-20 column as used in parts A. and B. of this Example, and the column was eluted with chloroform-methanol-hexane (65:10:25). After collecting the first 285 ml of the eluate in one portion, fractions of 13 ml were collected. The fractions were analyzed for antistaphylococcal activity as described in part A of this Example. The results are listed in the table.

| Fraction number | Zone of inhibition |
| --- | --- |
| 1 | 15 |
| 2 | 20 |
| 3 | 29 |
| 4 | 30 |
| 5 | 26 |
| 6 | 24 |
| 7 | 20 |
| 8 | 20 |
| 9 | 20 |
| 10 | 22 |
| 11 | 22.5 |
| 12 | 31.5 |

-continued

| Fraction number | Zone of inhibition |
| --- | --- |
| 13 | 29.5 |
| 14 | 30 |
| 15 | 30.5 |
| 16 | 30 |
| 17 | 25 |
| 18 | 18 |
| 19 | 17 |
| 20 | 0 |

The results of this Example thus show that, although the components of the PR-1350 complex can be at least partly separated, the isolated components are rapidly transformed into the original PR-1350 complex.

What we claim is:

1. A complex of closely related compounds, this complex being designated PR-1350 and hemiacetals thereof with alcohols of the general formula ROH, R being represented by a straight or branched alkyl radical having from 1 to 8 carbon atoms, such alkyl radicals being optionally substituted with halogen atoms or hydroxy, alkyloxy, aralkyloxy, aryloxy, alkanoyloxy, aralkanoyloxy, aroyloxy, sulfhydryl, alkylthio, aralkylthio, arylthio, alkanoylthio, aroylthio, azido, nitro, cyano, thiocyano, hydroxycarbonyl, alkyloxycarbonyl, aryloxycarbonyl, amino, alkylamino, dialkylamino, arylamino, alkanoylamino, and aroylamino groups; R can further be an alkenyl or alkynyl radical having from 2 to 6 carbon atoms, a cycloalkyl radical having from 3 to 7 carbon atoms in the alicyclic ring, or the mono- or dihalo, lower alkyl, lower alkoxy or hydroxy substituted analogues, an aralkyl, heterocyclylalkyl or aryl radical, these radicals being optionally substituted with halogen, nitro, lower alkyl, hydroxy or alkoxy radicals, PR-1350 having the basic structure as shown in formula I

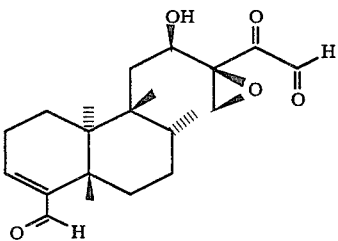

and the complex PR-1350 being characterized by the following physico-chemical properties:

1. IR-spectrum of PR-1350: as shown in FIG. 1;
2. Optical rotation of PR-1350, measured 4 hours after preparation of the solution: $[\alpha]_D^{20} = +85°-90°$ (c=1, ethanol);
3. Electron impact mass spectrum (m/e) or PR-1350: 366, 205, 204, 189, 187, 175, 161, 159, 149, 147, 145, 135, 133, 131, 121, 119, 109, 107, 105, 95, 93, 91, 81, 79, 77, 69, 67, 55, 44, 41;
4. $^1$H-NMR spectrum (10% solution deuteroacetone) of PR-1350: 9.28 (s), 6.63 (bt), 2.41 (m), 1.77 (m), 1.21 (s), 0.96 (s);
5. $^{13}$C-NMR spectrum (10% solution in deuterochloroform) of PR-1350: 193.8 (d), 151.9 (s), 151.5 (d), 44.1, 37.6, 36.3, 29.3, 28.6, 25.9, 21.6, 17.8, 15.8;
6. Ultraviolet absorption maximum at 230 nm ($E_1\ cm^{1\%} = 304$) of PR-1350 in ethanol solution;
7. Solubility of PR-1350: Soluble in ethyl acetate, ethyl ether, benzene, ethanol, methanol, and chloroform; relatively insoluble in water; and insoluble in saturated hydrocarbon solvents.

2. A substance according to claim 1 and being a hemiacetal of PR-1350 with methanol, this substance being designated PR-1381, having the formula II

Figure 2:
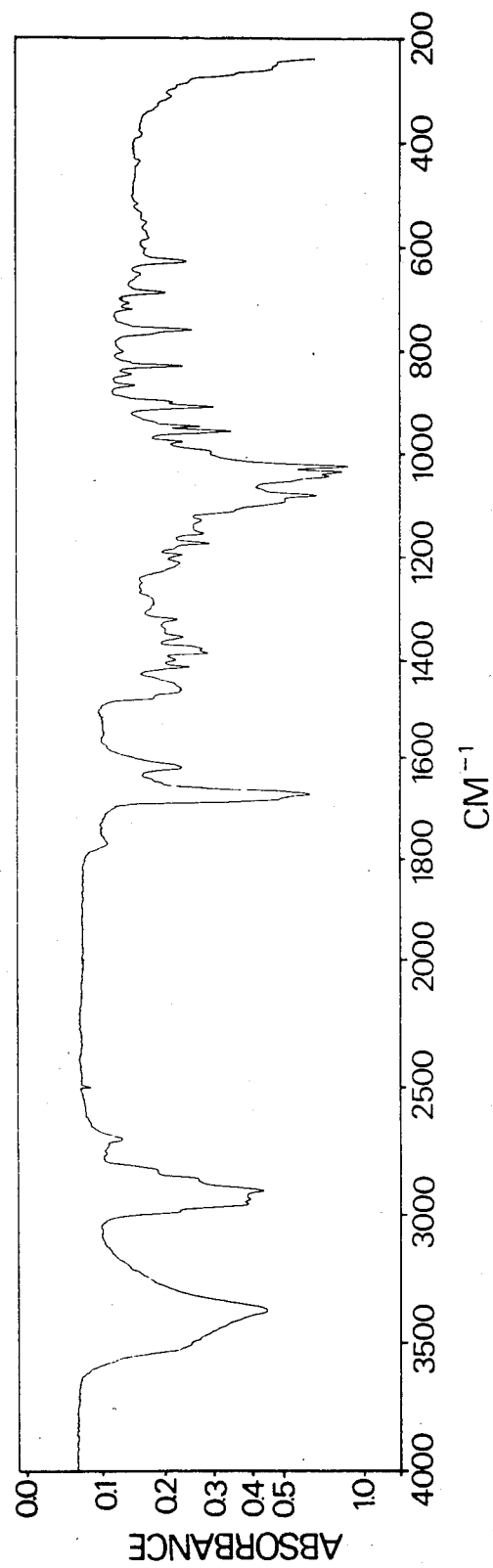

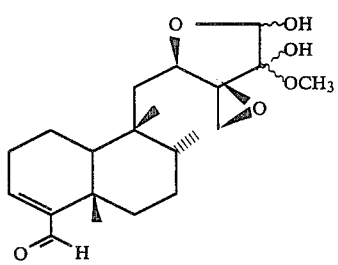

and possessing the following physico-chemical characteristics:

1. Elemental analysis: C: 66.30, H: 8.50;
2. Melting point: 139°-141° C.;
3. IR spectrum as shown in FIG. 2;
4. Specific rotation (c=0.2, ethanol) 0 hours after preparation: $[\alpha]_D^{20} = +102.8°$;
5. Specific rotation (c=0.2, ethanol) 10 hours after preparation: $[\alpha]_D^{20} = +89.6°$;
6. Electron impact mass spectrum (m/e): identical with the spectrum of PR-1350 according to claim 1;
7. $^1$H-NMR spectrum recorded immediately after preparation of a 10% solution in deuterochloroform; 9.28 (s), 6.54 (t), 5.31 (bs), 4.58 (t), 3.40 (s), 3.25 (d, J=4.5), 2.82 (d, J=4.5), 2.35 (m), 1.77 (m), 1.21 (s), 1.00 (d, J=6), 0.90 (s);
8. Ultraviolet absorption maximum at 230 nm ($1_1\ cm^{1\%} = 310$) in ethanol solution.

3. A substance as claimed in claim 1 in substantially pure form.

4. A method for producing a hemiacetal, according to claim 1, comprising mixing the PR-1350 complex and an alcohol of the formula ROH as defined in claim 1.

5. A method for producing the hemiacetal PR-1381, according to claim 2, which comprises dissolving the PR-1350 complex in methanol and isolating the crystalline product by filtration.

6. Method for producing the PR-1350 complex according to claim 1, in which a hemiacetal of PR-1350 is dissolved in an organic solvent different from ROH as defined in claim 1, leaving the solution for a suitable time and precipitating the thus formed PR-1350 complex.

7. A pharmaceutical composition for human or veterinary use comprising as active ingredient a substance as defined in claim 1, together with pharmaceutically acceptable, non-toxic carriers and/or auxiliary agents.

8. A therapeutic method for treating an infectious disease which comprises administering to a host in need of such treatment an effective amount of a complex according to claim 1.

* * * * *